(12) United States Patent
Lange et al.

(10) Patent No.: US 10,539,360 B2
(45) Date of Patent: Jan. 21, 2020

(54) FREEZING MACHINE WITH CONTAINER FOR FROZEN SAMPLES

(71) Applicant: Leica Mikrosysteme GmbH, Vienna (AT)

(72) Inventors: Robert Lange, Vienna (AT); Cveta Tomova, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 145 days.

(21) Appl. No.: 15/526,355

(22) PCT Filed: Nov. 13, 2014

(86) PCT No.: PCT/EP2014/074425
§ 371 (c)(1),
(2) Date: May 12, 2017

(87) PCT Pub. No.: WO2016/074720
PCT Pub. Date: May 19, 2016

(65) Prior Publication Data
US 2017/0328629 A1    Nov. 16, 2017

(51) Int. Cl.
*F25D 29/00* (2006.01)
*F25D 3/10* (2006.01)
(Continued)

(52) U.S. Cl.
CPC .......... *F25D 29/001* (2013.01); *A01N 1/0268* (2013.01); *A01N 1/0289* (2013.01);
(Continued)

(58) Field of Classification Search
CPC . F25D 29/001; F25D 3/10; F25D 3/11; F25D 29/00; F25D 3/00; G01N 1/42; G01N 1/00; A01N 1/0289; A01N 1/0268
See application file for complete search history.

(56) References Cited

U.S. PATENT DOCUMENTS

| 4,723,420 A | 2/1988 | Sitte | |
|---|---|---|---|
| 5,205,128 A * | 4/1993 | Richard | A01N 1/02 62/441 |
| 2009/0133410 A1 | 5/2009 | Thorne et al. | |

FOREIGN PATENT DOCUMENTS

| JP | H06509782 A | 11/1994 |
|---|---|---|
| JP | H10-243951 A | 9/1998 |

(Continued)

OTHER PUBLICATIONS

Leica Microsystems, Leica EM HPM100, Brochure, 12 pages Mar. 8, 2009.

*Primary Examiner* — Emmanuel E Duke
(74) *Attorney, Agent, or Firm* — Hodgson Russ LLP

(57) ABSTRACT

The invention relates to a freezing machine (150) for freezing samples, encompassing: a freezing device (140) for freezing a sample received in the freezing machine (150); a container (100) for receiving the frozen sample, having a reservoir (105) for liquid nitrogen; and a transfer apparatus for transferring the frozen sample from the freezing device (140) into the container (100), the container (100) comprising at least two receiving devices (104), separated from one another, each for at least one frozen sample; a selection apparatus being provided for selecting one of the receiving devices (104) for a frozen sample that is to be transferred into the container (100), the freezing machine (150) being configured to carry out the transfer of the frozen sample, by means of the transfer apparatus, into the respectively selected receiving device (104) of the container (100); and to a method for transferring frozen samples into a container provided therefor.

10 Claims, 7 Drawing Sheets

(51) Int. Cl.
  *A01N 1/02*  (2006.01)
  *G01N 1/42*  (2006.01)
  *F25D 3/00*  (2006.01)
  *G01N 1/00*  (2006.01)
(52) U.S. Cl.
  CPC ................ *F25D 3/10* (2013.01); *G01N 1/42* (2013.01); *F25D 3/00* (2013.01); *F25D 29/00* (2013.01); *G01N 1/00* (2013.01)

(56) References Cited

FOREIGN PATENT DOCUMENTS

| | | |
|---|---|---|
| JP | 2005-156136 A | 6/2005 |
| JP | 2011019564 A | 2/2011 |

\* cited by examiner

FREEZING MACHINE WITH CONTAINER FOR FROZEN SAMPLES

CROSS-REFERENCE TO RELATED APPLICATIONS

The present application is the U.S. national phase of International Application No. PCT/EP2014/074425 filed Nov. 13, 2014, which is incorporated herein by reference in its entirety.

FIELD OF THE INVENTION

The present invention relates to a freezing machine, in particular a high-pressure freezing machine, having a container for receiving frozen samples; and to a method for transferring frozen samples into such a container.

BACKGROUND OF THE INVENTION

The freezing of samples, in particular under high pressure, is a widely used method for preparing samples, for example for viewing under an electron microscope. This high-pressure freezing makes it possible to view water-containing biological and industrial samples in close to their original state. For example, freezing at pressures of approximately 2000 bar suppresses the formation of ice crystals and avoids structural damage to the sample. The process is referred to as "vitrification," i.e. the solidification of a liquid by elevating its viscosity while it is being cooled: crystallization is absent, and an amorphous material thus results. This is achieved by extremely rapid cooling (e.g. in liquid nitrogen), usually in interaction with additives that prevent crystallization (called "cryoprotectives").

Freezing machines, in particular high-pressure freezing machines, that are used for the above-described freezing of samples are obtainable. These freezing machines do make it possible to freeze a sample, but the problem of further handling then arises, since the cold chain should if possible not be interrupted.

A freezing machine is available from the Applicant under the designation "Leica EM HPM100"; it encompasses for this purpose a container, cooled with liquid nitrogen, into which the samples are automatically introduced after the freezing operation. This does initially allow the cold chain to be ensured, but there is no possibility of sorting or tracking samples introduced into the container. Freezing of different samples in series is thus not possible or possible only with additional outlay.

A further problem that results in the context of freezing in series is that the supply of liquid nitrogen present in the container may not last until the end of the series. The series may therefore need to be interrupted in order to refill the container with liquid nitrogen.

The object that presents itself is therefore that of describing a capability for allowing simple execution even of longer series of freezing operations of samples, in particular also including different samples.

SUMMARY AND ADVANTAGES OF THE INVENTION

According to the present invention a freezing machine and a method having the features described herein are proposed. Advantageous embodiments are the subject matter of the description which follows.

A freezing machine according to the present invention serves to freeze samples. The freezing machine encompasses for that purpose: a freezing device for freezing a sample received in the freezing machine; a container for receiving the frozen sample, having a reservoir for liquid nitrogen; and a transfer apparatus for transferring the frozen sample from the freezing device into the container. The container comprises at least two receiving devices, separated from one another, each for at least one frozen sample; and a selection apparatus is provided for selecting one of the receiving devices for a frozen sample that is to be transferred into the container. The freezing machine is configured to carry out the transfer of the frozen sample, by means of the transfer apparatus, into the respectively selected receiving device of the container.

A freezing machine of this kind, which in particular is a high-pressure freezing machine, makes it possible to introduce various samples separately, after the respective freezing operation, into a cooled container in simple and rapid fashion with no need to interrupt a series of freezing operations, for example in order to change the container, for example when changing from one sample type to another. The ability to associate a sample with the respective freezing operation is obtained because of the at least two separate receiving devices in the container.

Preferably the at least two receiving devices are arranged shiftably and/or rotatably in the container. On the one hand, the receiving devices can thereby easily be relocated in the container, for example beneath an ejector of the freezing machine; on the other hand, a conventional freezing machine at least having a conventional freezing device and transfer apparatus can continue to be used, and physical reconfiguration can be limited to the region after sample ejection.

Advantageously, the selection apparatus comprises drive means by means of which the at least two receiving devices are shiftable and/or rotatable. The drive means can in particular comprise a motorized drive system. This enables particularly simple and convenient positioning.

It is advantageous if the freezing machine is configured to automatically position the receiving device selected for the sample that is to be transferred, in such a way that the sample is transferred into the receiving device. A series of freezing operations with different samples can thereby be carried out particularly simply and rapidly.

It is advantageous if the at least two receiving devices are removable from the container. This makes possible simple further treatment of the individual samples, for example after removal of the container from the freezing machine. In order to retain association capability, the receiving devices usefully are distinguishable, for example numbered or otherwise characterized.

It is furthermore advantageous if the freezing machine is configured to associate a receiving device filled with a sample with the freezing operation of the sample, and to store and/or output the association. This enables immediate and/or subsequent trackability of the association. Especially in combination with the aforementioned characterization of the receiving device, rapid and reliable execution of freezing operations of different samples is enabled.

The freezing machine is preferably configured for automatic filling of the reservoir with liquid nitrogen. A longer series of freezing operations can thus be carried out with no need for possible manual refilling with liquid nitrogen. Means for monitoring the fill level of the liquid nitrogen can also be provided on the container, for example for additional checking.

A method according to the present invention serves for transferring frozen samples into a selected receiving device of a container that is provided therefor and encompasses at least two receiving devices separated from one another. In this context, one of the receiving devices is selected, and a sample is transferred into the selected receiving device after a pertinent freezing operation. Advantageously, the selected receiving device is positioned, by shifting and/or rotating, for transfer of the sample. It is also useful if the selected receiving device is associated with the sample and/or with a freezing operation pertinent to the sample, and if the association is stored and/or outputted.

To avoid repetition, with regard to the advantages of the method according to the present invention reference is made to the statements above regarding the freezing machine according to the present invention.

Further advantages and embodiments of the invention are evident from the description below and from the appended drawings.

It is understood that the features recited above and those yet to be explained below are usable not only in the respective combination indicated but also in other combinations or in isolation, without departing from the scope of the present invention.

The invention is schematically depicted in the drawings on the basis of an exemplifying embodiment, and will be described in detail below with reference to the drawings.

BRIEF DESCRIPTION OF THE DRAWING VIEWS

DETAILED DESCRIPTION OF THE INVENTION

In the description below of the Figures, identical reference numbers identify identical parts; in the interest of clarity, not all reference numbers are depicted in each Figure.

Figure 1:
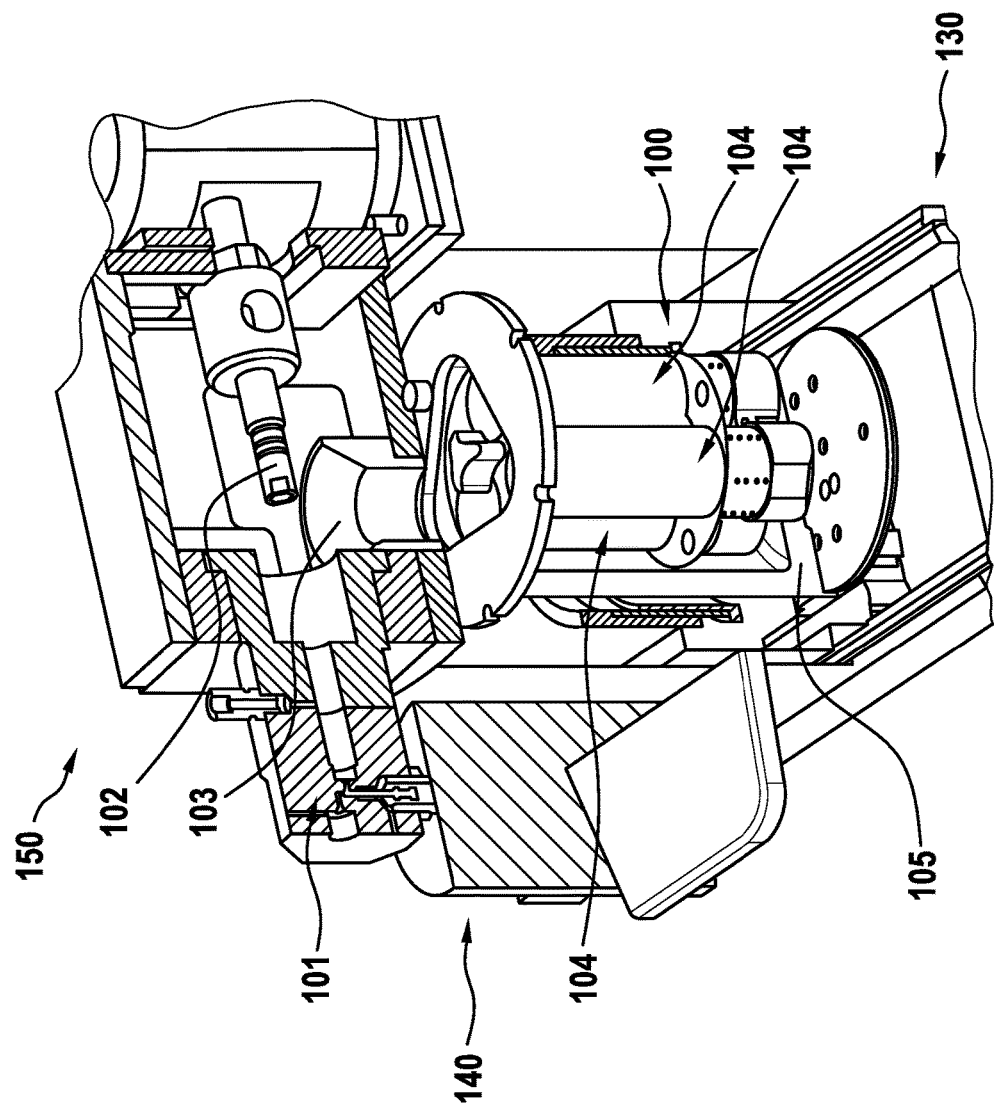
FIG. 1 shows a detail of a freezing machine according to the present invention having a container, in a preferred embodiment.

FIG. 1 shows a detail of a freezing machine 150 embodied as a high-pressure freezing machine. High-pressure freezing machine 150 encompasses a loading/unloading apparatus in the form of a slide-in apparatus 130. A container 100 having, in the present case, three receiving devices 104 is placed on slide-in apparatus 130. Note in this connection that the number of receiving devices in the present case is merely exemplifying. Only two, or also four or more, receiving devices are likewise conceivable.

High-pressure freezing machine 150 furthermore encompasses a freezing device 140 having a high-pressure chamber 101; in the interest of clarity, elements for pressure generation when liquid nitrogen is used are not depicted. A sample that is to be frozen under high pressure is positioned in a holder (in particular, a sample cassette) in gripper 102. For a more detailed description of the positioning of a sample in the gripper, reference is made at this juncture to FIG. 3. The gripper can be slid via a pneumatic piston into high-pressure chamber 101.

Figure 4:
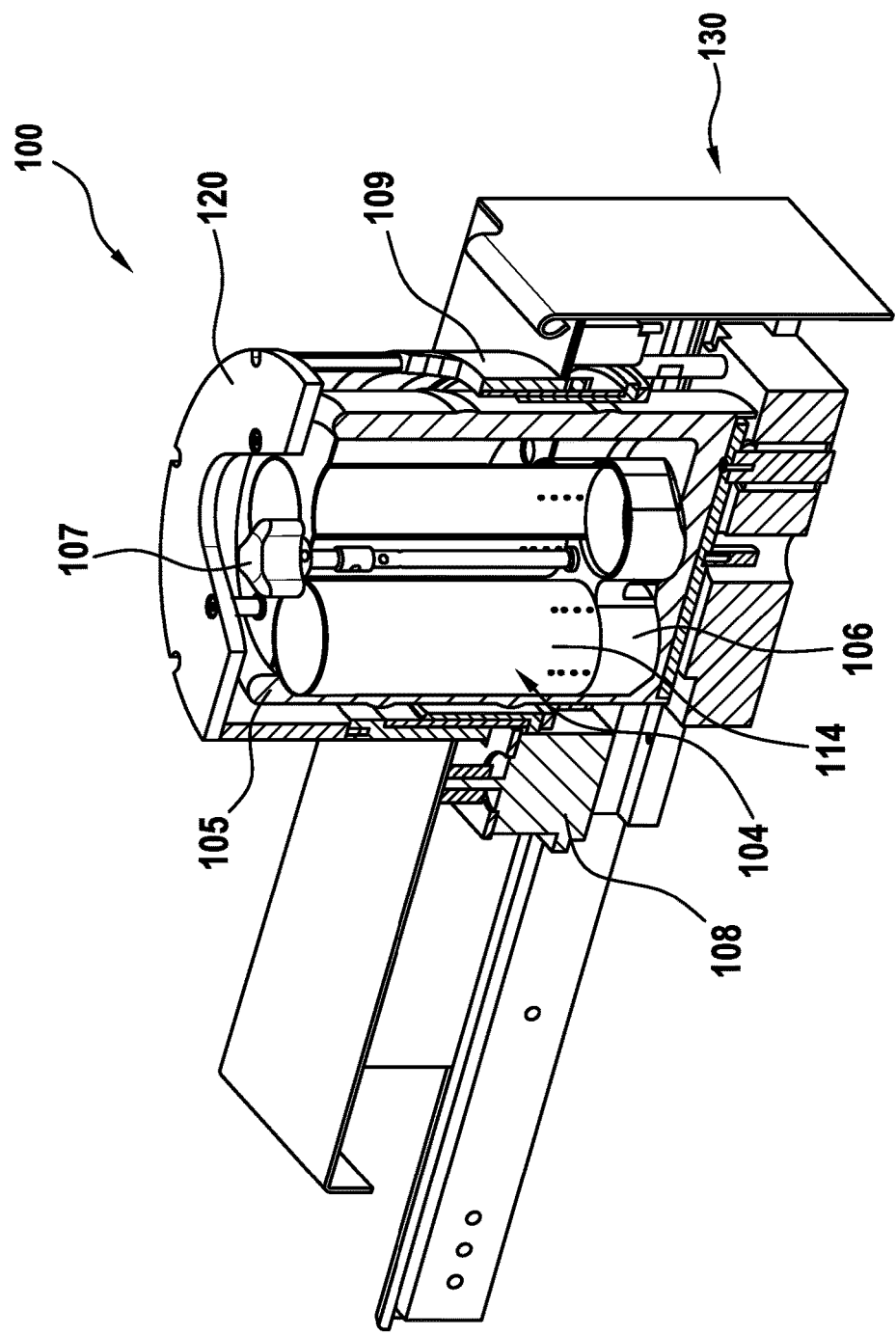
FIG. 4 shows the container of a freezing machine according to the present invention in a preferred embodiment.
Figure 5:
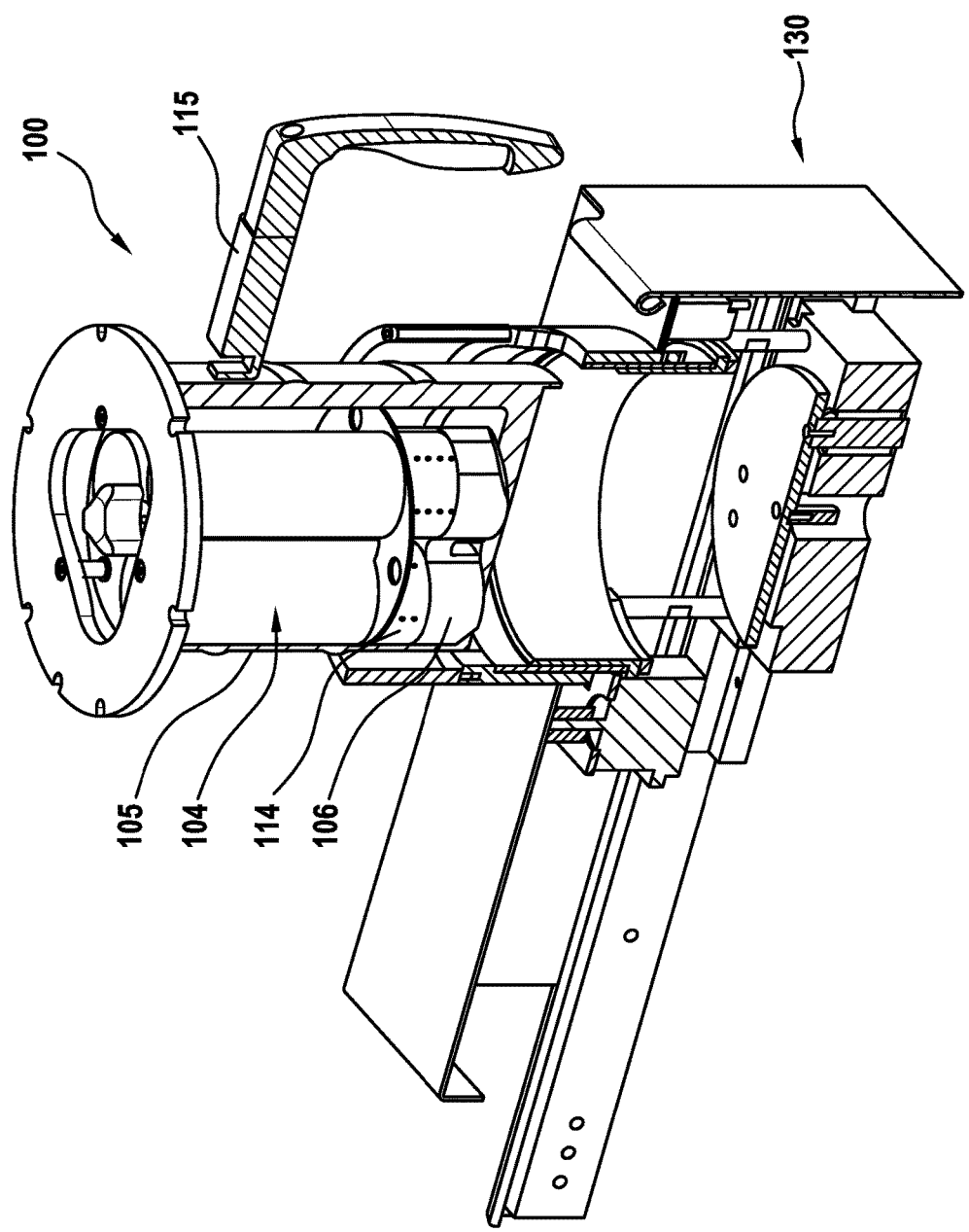
FIG. 5 shows the container of FIG. 4 in a different working position.
Figure 6:
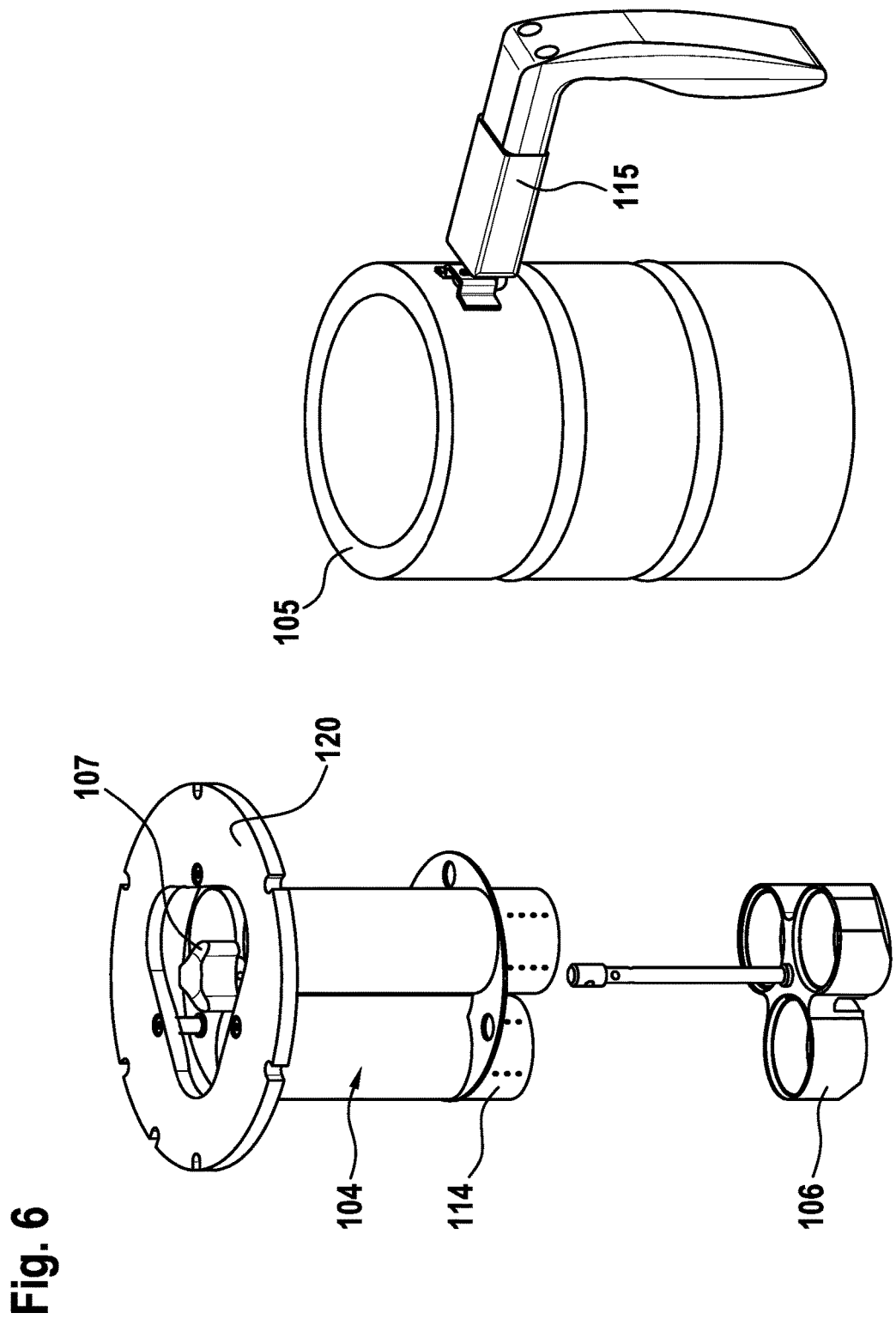
FIG. 6 shows the container of FIGS. 4 and 5 with receiving devices separate from the reservoir for liquid nitrogen.

Gripper 102 is depicted in FIG. 1 in an ejection position, this being a working position after a freezing operation. A mechanism for releasing the sample, e.g. a movable peg for pushing the sample out of the gripper, is not shown here in the interest of clarity. A collection funnel 103 directs a dropping sample into one of receiving devices 104. In the embodiment depicted, receiving devices 104 can be automatically rotated so that one of receiving devices 104 can be selected for a sample to be transferred into the container. Reference is made to FIGS. 4 to 6 for a further description of container 100.

Freezing machine 150 is furthermore configured to correlate the receiving device into which a sample is transferred with the sample and/or with the corresponding freezing operation. Association and trackability are thus ensured. This correlation can be carried out, for example, by means of a computation unit in which, for example, a list, having an association as to which sample is located in which receiving device, is stored. The correlation can also be outputted, for example, via a display and/or a printer. It is of course also conceivable in this context to introduce more than one sample into a receiving device. Corresponding sequences can, for example, be programmed on freezing machine 150 for this, and for transfer into the receiving devices (optionally including the freezing operation).

Figure 2:
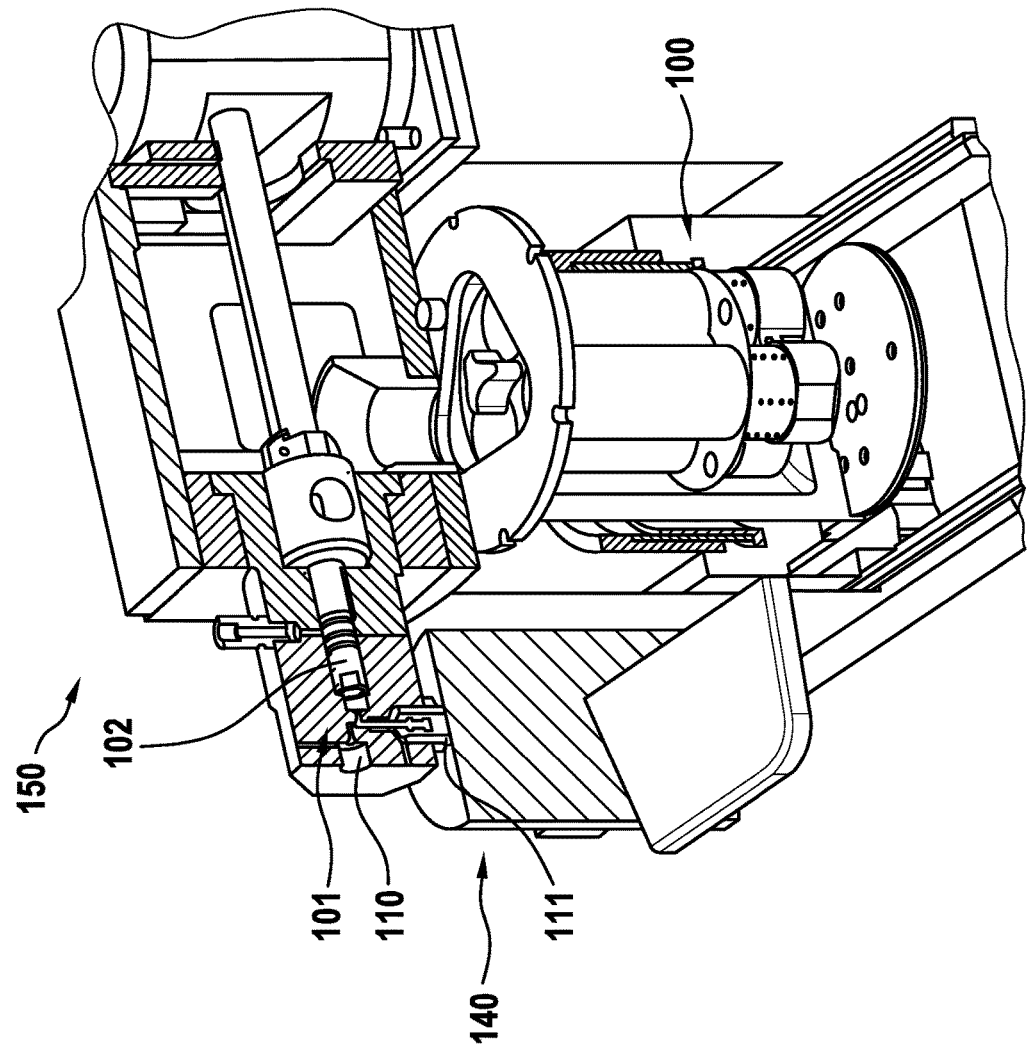
FIG. 2 shows the detail of FIG. 1 in a different working position.

FIG. 2 shows the same detail of high-pressure freezing machine 150 as in FIG. 1. Gripper 102 is in a different working position, however: it is slid into high-pressure chamber 101. In the freezing operation, after a valve 111 is opened liquid nitrogen is forced under high pressure (approx. 2000 bar) via a supply line 110 into high-pressure chamber 101, and freezes the sample located in the high-pressure chamber.

Figure 7:
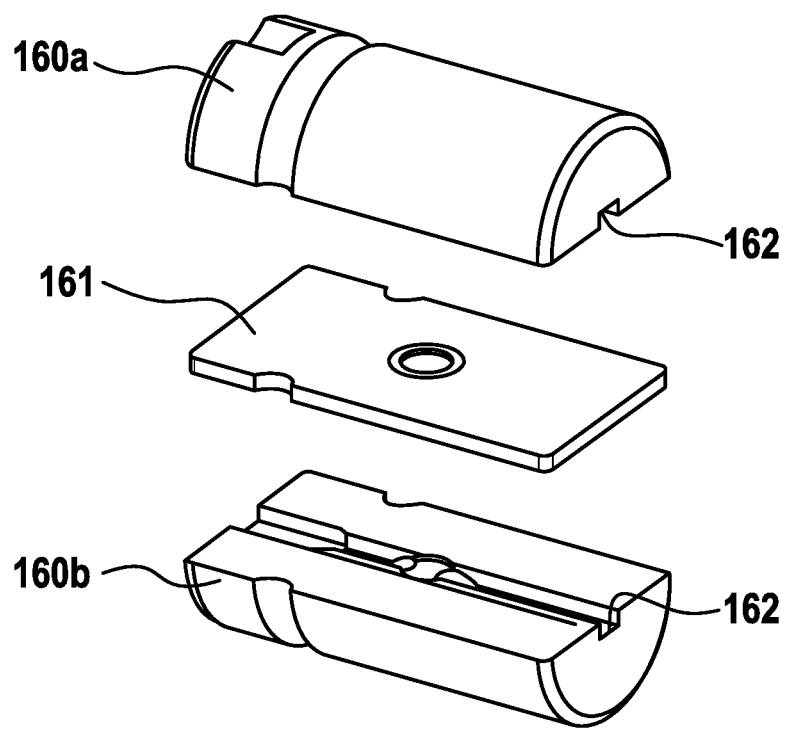
FIG. 7 shows an example of a sample cassette having a specimen slide, for use in a freezing machine according to the present invention.

FIG. 3 again shows the same detail of high-pressure freezing machine 150 as in FIG. 1. Here, however, gripper 102 is in a loading position for receiving a new sample. A sample is delivered for this purpose from the front; this is accomplished in particular manually by an operator of the high-pressure freezing machine. The freezing machine usually comprises for this purpose a working plate (table) on which the operator can prepare the samples and place them onto a sample carrier (e.g. specimen slide). A microscope, which makes it easier for the operator to process, prepare, and transfer the samples onto the specimen slides, can be provided for this purpose, for example, on the high-pressure freezing machine, but automatic delivery of the sample is also conceivable. The specimen slide having the sample is then usually introduced into a sample cassette. The sample cassette can be part of the gripper or can be gripped by the gripper. An exemplifying sample cassette is made up of two cylinder halves having channels for the liquid nitrogen, the specimen slide being immobilized between the two cylinder halves. Reference is made to FIG. 7 for a more detailed description of the sample cassette.

Figure 3:
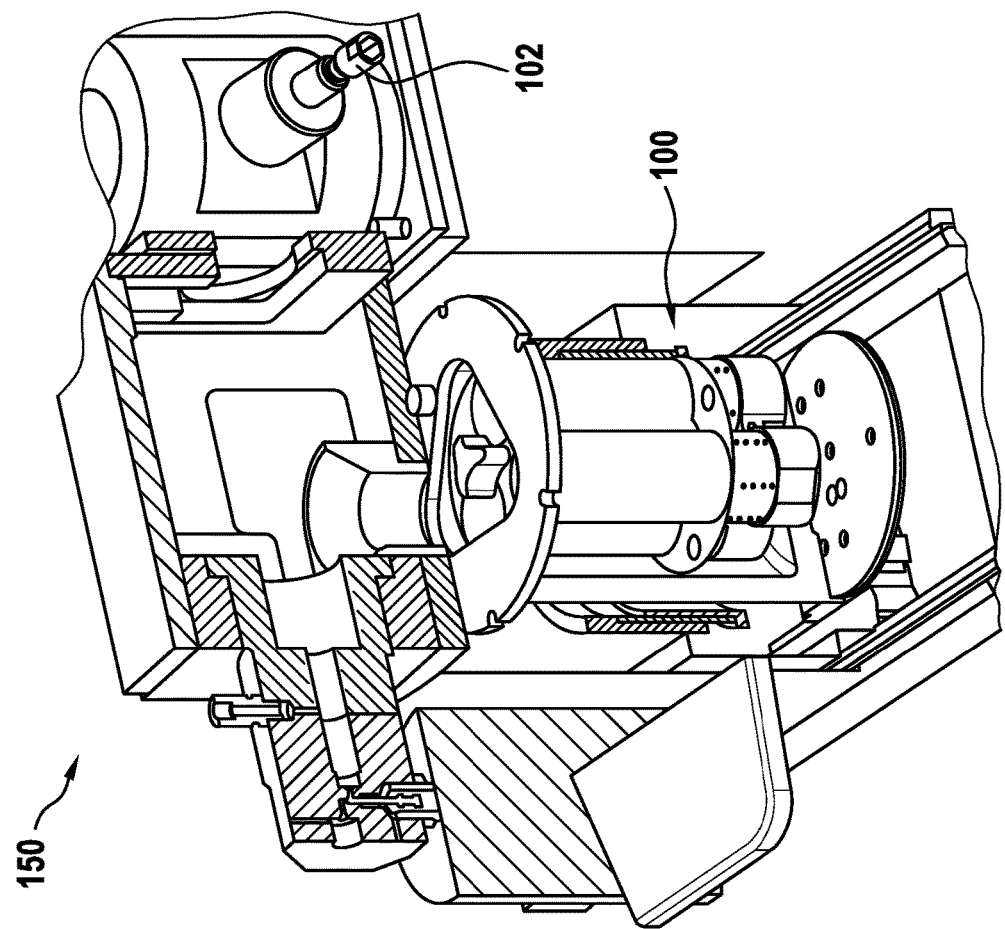
FIG. 3 shows the detail of FIGS. 1 and 2 in a further working position.

In order to freeze the sample, gripper 102 having the sample cassette is now, in the high-pressure freezing machine depicted in FIGS. 1 to 3, rotated approximately 90° clockwise around a vertical axis and then pushed toward high-pressure chamber 101 by means of the pneumatic piston. The sample cassette having the sample is thereby slid into high-pressure chamber 101, and gripper 102 closes off the high-pressure chamber in pressure-tight fashion. In order to switch between the various working positions, gripper 102 is equipped, for example, with an electrical drive system with which it is rotatable around the vertical axis.

As mentioned above, liquid nitrogen is then introduced under high pressure into high-pressure chamber 101 and penetrates through the channels of the sample cassette to the sample, which freezes as a result. The sample cassette is then taken back out of high-pressure chamber 101 by gripper 102, by means of the pneumatic piston. Gripper 102 then travels into the ejection position depicted in FIG. 2, and the sample cassette having the sample can be transferred into container 100 or into one of receiving devices 104 of container 100. In the present case, the sample is transferred in simple fashion by the fact that the sample cassette is ejected from the gripper and then, as already mentioned above, drops and is directed via funnel 103 into container 100 or into the correspondingly positioned receiving device 104.

FIG. 4 depicts the loading/unloading apparatus or slide-in apparatus 130 having container 100. Said apparatus is embodied as a motorized drawer that can be moved out of and into the freezing machine.

A motor 108 is provided in order to rotate, by means of belts, an outer ring 109 that in turn is connected via a plate 120 to receiving devices 104. A connection between the outer ring and plate 120 is created via screws, protruding from the outer ring, which engage into corresponding recesses on the rim of plate 120. A reservoir or "dewar" 105 for receiving liquid nitrogen remains in a fixed position during the rotation.

Receiving devices 104 are arranged in dewar 105 filled with liquid nitrogen. The filling of dewar 105 with liquid nitrogen is accomplished in the present case automatically, using a filling apparatus (not further depicted here). As already mentioned previously, the number of samples that can be frozen in series is increased by such automatic filling of dewar 105. Automatic filling makes it possible to omit an indication of the fill level of the liquid nitrogen, which is usually provided in the context of previously utilized containers having a dewar. Such an indication can, however, continue to be provided for safety reasons.

FIG. 5 again depicts slide-in apparatus 130 having container 100, but container 100 encompassing dewar 105, receiving devices 104 made up of receiving vials 114 and a base 106, and a plate 12, are shown in a raised position, i.e. in a removal position. A handle 115 attachable to dewar 105 can be used, for example, for removal. It is understood that for removal, slide-in apparatus 130 having container 100 must be located in a position that is extended out from the freezing machine as compared with the transfer of samples.

FIG. 6 shows dewar 105 with handle 115 for removal, separately from an insert having receiving vials 114 and the corresponding base 106. Base 106 is detachably connected to receiving vials 114 via a screw 107. Receiving vials 114, together with base 106 that comprises the segments corresponding to receiving vials 114, constitute receiving devices 104.

For removal of the samples from receiving devices 104, dewar 105 is raised and, for example, conveyed into an external manipulation vessel (for example, a Styrofoam box filled with liquid nitrogen). Screw 107 is then loosened. The samples are removed from base 106 or from its individual segments. The segments of base 106, constituting a part of receiving devices 104, are internally numbered and have a unique mechanical connection to plate 120. A unique association of samples, or their freezing operations, with the receiving devices is thus retained, in particular together with the association carried out by the freezing machine.

FIG. 7 shows an exemplifying sample cassette made up of top cylinder half 160a and bottom cylinder half 160b. Specimen slide 161, having the sample placed at the center of the specimen slide, is introduced into sample cassette 160a, 160b, i.e. between the two cylinder halves.

Sample cassette 160a, 160b can then be gripped by gripper 102 and introduced into high-pressure chamber 101. The two cylinder halves 160a and 160b comprise channels 162 through which liquid nitrogen can travel to the sample placed on specimen slide 162.

What is claimed is:

1. A freezing machine (150) for freezing samples, comprising:
    a freezing device (140) for freezing a sample received in the freezing machine (150);
    a container (100) for receiving the frozen sample, having a reservoir (105) for liquid nitrogen; and
    a transfer apparatus for transferring the frozen sample from the freezing device (140) into the container (100), wherein the container (100) comprises at least two receiving devices (104), separated from one another, each for at least one frozen sample, the at least two receiving devices (104) being arranged shiftably and/or rotatably in the container (100);
    a motor (108) operable to shift and/or rotate the at least two receiving devices (104) to position one of the receiving devices (104) for a frozen sample that is to be transferred into the container (100) correspondingly with respect to the transfer apparatus,
    the freezing machine (150) being configured to carry out the transfer of the frozen sample, by means of the transfer apparatus, into the correspondingly positioned receiving device (104) of the container (100).

2. The freezing machine (150) according to claim 1, the selection apparatus comprising drive means (108, 109) by means of which the at least two receiving devices (104) are shiftable and/or rotatable.

3. The freezing machine (150) according to claim 1, the freezing machine (150) being configured to automatically position the receiving device (104), selected for the sample that is to be transferred, such that the sample is transferred into the receiving device.

4. The freezing machine (150) according to claim 1, the at least two receiving devices (104) being removable from the container (100).

5. The freezing machine (150) according to claim 1, the freezing machine (150) being configured to associate the receiving device (104), selected for the sample that is to be transferred, with the sample and/or with a freezing operation pertinent to the sample, and to store and/or output the association.

6. The freezing machine (150) according to claim 1, the freezing machine (150) being configured for automatic filling of the reservoir (105) with liquid nitrogen.

7. A method for transferring frozen samples in a freezing machine (150) into a selected receiving device (104) of a container (100) of the freezing machine (150) which is provided therefor and comprises at least two receiving devices (104) separated from one another, the method comprising: selecting one of the at least two receiving devices (104), automatically positioning the selected receiving device (104) for transfer of a sample by shifting and/or rotating the selected receiving device (104) using a motor (108), and automatically transferring the sample into the selected receiving device (104) after the sample is frozen by a freezing operation.

8. The method according to claim 7, the selected receiving device (104) being automatically associated with the sample and/or with a freezing operation pertinent to the sample, and the association being stored and/or outputted.

9. The method according to claim 7, wherein the freezing machine (150) comprises a freezing device (140) for freezing the sample, a transfer apparatus for transferring the frozen sample from the freezing device (140) into the container (100), and a selection apparatus for selecting one of the receiving devices (104) for the frozen sample, wherein the frozen sample is automatically transferred into the selected receiving device (104) after the pertinent freezing operation by the transfer apparatus.

10. A freezing machine (150) for freezing samples, comprising:
- a freezing device (140) for freezing a sample received in the freezing machine (150);
- a container (100) for receiving the frozen sample, having a reservoir (105) for liquid nitrogen, the freezing machine (150) being configured for automatic filling of the reservoir (105) with liquid nitrogen; and
- a transfer apparatus for transferring the frozen sample from the freezing device (140) into the container (100);
- wherein the container (100) comprises at least two receiving devices (104), separated from one another, each for at least one frozen sample;
- a motor (108) operable to shift and/or rotate the at least two receiving devices (104) to position one of the receiving devices (104) for a frozen sample that is to be transferred into the container (100) correspondingly with respect to the transfer apparatus, and
- the freezing machine (150) being configured to carry out the transfer of the frozen sample, by means of the transfer apparatus, into the correspondingly positioned receiving device (104) of the container (100).

* * * * *